United States Statutory Invention Registration [19]

[11] Reg. Number: H473

Lester et al.

[43] Published: Jun. 7, 1988

[54] CAPILLARY TUBE SCANNER

[75] Inventors: Robert S. Lester; Charles E. Smith, both of Houston; Timothy C. Hurley, Stafford; Terrence A. Onda, Houston, all of Tex.

[73] Assignee: Shell Oil Company, Houston, Tex.

[21] Appl. No.: 689,752

[22] Filed: Jan. 9, 1985

[51] Int. Cl.[4] ..... G01N 15/02; G01N 21/01; C12Q 1/18

[52] U.S. Cl. ..... 356/335; 356/244; 435/32

[58] Field of Search ..... 356/335, 244

[56] References Cited

U.S. PATENT DOCUMENTS

| | | | |
|---|---|---|---|
| 3,275,834 | 9/1966 | Stevens | 356/335 |
| 3,574,063 | 4/1971 | Bowman | 435/30 |
| 3,694,317 | 9/1972 | Scher | 356/244 |

*Primary Examiner*—Stephen C. Buczinski
*Assistant Examiner*—Linda J. Wallace

[57] ABSTRACT

A method and apparatus for counting small particles in a capillary tube is provided. The method and apparatus detect changes in the intensity of the direct beam passing perpendicularly through the capillary tube to count such small particles.

13 Claims, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CAPILLARY TUBE SCANNER

BACKGROUND OF THE INVENTION

The present invention relates to a method and apparatus for scanning capillary tubes for minute particles, and more particularly, relates to a method and apparatus for scanning capillary tubes to count very small biological materials and particles, to determine the chemical activity of such particles.

In the diagnosis and treatment of human cancer, a recurring problem is the timely selection of the most effective chemotherapeutic agent against an individual tumor. A system that quickly clones a human tumor to provide multiple specimens for testing of the various chemotherapeutic agents for effectivity has the potential for predicting which drug will be effective against a specific tumor.

The conventional two layer soft agar system for such cloning has a variety of problems that render this system ineffective. These problems include the inability to grow the majority of patients' tumors, the need for a large number of tumor cells, the large amount of technical time and expense for plating and counting, and the lack of flexibility for utilizing different drug schedules or combinations of drugs.

This conventional two layer soft agar system usually employs 35 mm petri dishes. However, the use of capillary tubes has increased the success rate of tumor growth beyond that of the petri dishes. To detect and count the tumor cell growth in petri dishes, there are commercially available image analyzers. Since the capillary technique appears to be more successful, there is a need for an automated apparatus for detection and counting of capillary clone colonies.

The equipment that is known or commercially available is not fully automated or not well suited for this application or related applications because of expense or reliability problems. This type of equipment is typified by U.S. Pat. No. 3,574,063 to Bowman. Such equipment usually detects a scattered beam with a very sensitive photomultiplier tube. These photo multiplier tubes are very fragile in nature and are susceptible to damage or reduced sensitivity with routine handling and use.

These and other limitations and disadvantages of the prior art are overcome by the present invention, however, and improved methods and apparatus are provided for detecting and measuring minute particles in capillary tubing.

SUMMARY OF THE INVENTION

In a preferred embodiment of the present invention, an improved capillary tube scanning apparatus and method is provided. The preferred embodiment of the present invention is an automated capillary scanning device that employs an improved light source, an iris or slit system on the condenser stage of the apparatus, a computer for storing and analyzing data and for controlling an improved sample positioner, an improved capillary tube for use in the sample positioner, and a photovoltaic absorption detector with its associated slit system and optics for detecting changes in intensity in the direct path light beam caused by small particles in a capillary tube to thereby count such small particles.

The preferred method of the present invention employs a suitable transparent container for holding small particles to be counted, a light source and appropriate optics to produce a beam of paraxial rays, and detects changes in direct beam intensity caused by the occlusion of such light by such small particles.

It is an object of the present invention to provide an improved capillary scanning apparatus.

It is also an object of the present invention to provide an improved method for counting small particles.

It is a further object of the present invention to provide an automated capillary scanning apparatus.

These and other objects and advantages of the present invention will become obvious based upon the following detailed description, wherein reference to the accompanying figures is made.

DESCRIPTION OF THE PREFERRED EMBODIMENT

Figure 1:
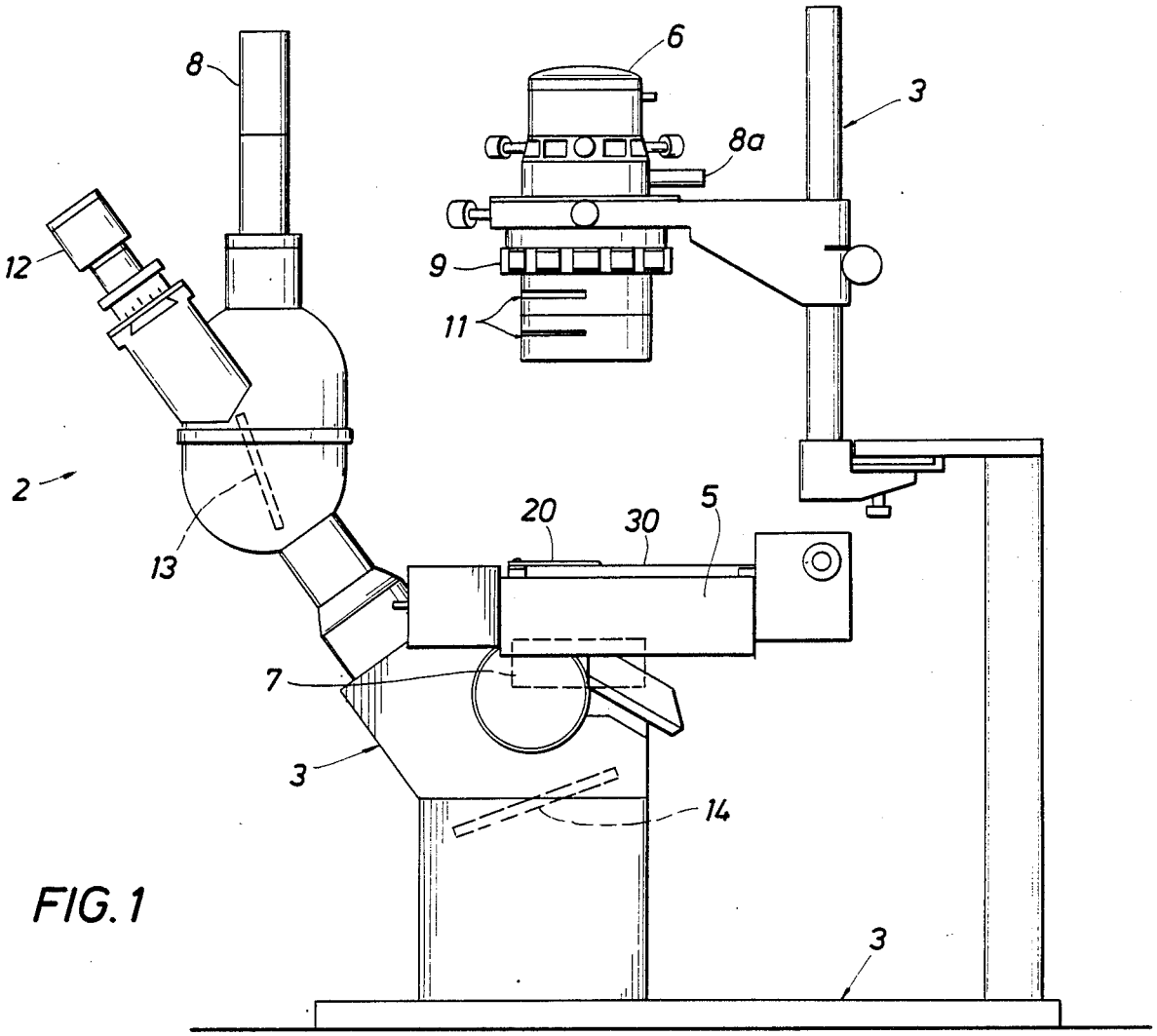
FIG. 1 depicts a side view of one embodiment of the apparatus of the present invention.

Referring now to FIG. 1, there may be seen a side view of a preferred embodiment of the present invention. This embodiment is a cell scanning apparatus 2 having a sample positioner or stage 5, a source 6, an objective lens 7 and detectors 8, 8*a*. There may also be seen an adjustable iris 9, a collimating lens 11 and an eyepiece 12 for operator viewing when mirror or prism 13 is moved to allow rays from the source 6 to enter the eyepiece 12. However, when mirror 13 is in the position depicted in FIG. 1 rays from source 6 enter the detector 8.

Continuing to refer to FIG. 1, there may also be seen a reflecting mirror 14 which serves to redirect rays from the source 6 toward the eyepiece 12 or detector 8 depending upon the position of mirror 13. The dashed lines for the objective lens 7, reflecting mirror 14 and mirror 13 to indicate the approximate locations of these items within apparatus 2. The hereinbefore described lenses (11, 7), source (6), iris (9), mirrors mirrors (13, 14), stage (5), detectors (8, 8*a*) and eyepiece (12) are all suitably attached to the frame 3 of apparatus 2.

Figure 2:
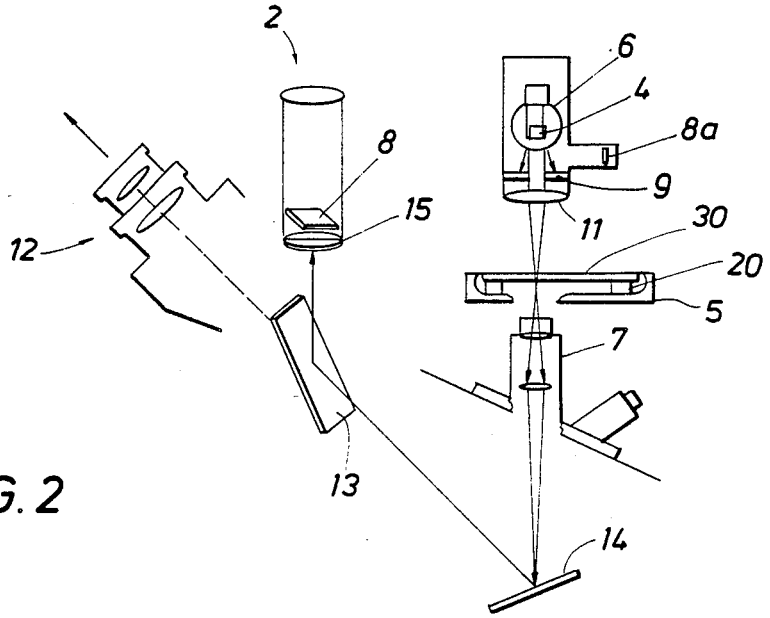
FIG. 2 depicts a schematic view of the apparatus of FIG. 1, partially in cross-section.

Referring now to FIG. 2 there may be seen a schematic view depicting the elements of the apparatus of FIG. 1, partially in cross-section. The arrangement of FIG. 2 more easily facilitates the explanation of the operation of the apparatus and method of the present invention.

Continuing to refer to FIG. 2, there may be seen a capillary tube holder 20 suitably arranged on stage 5 of the apparatus 2. Further, there may be seen a side view of one of a plurality of capillary tubes 30 in holder 20. In this manner capillary tubes 30 containing small particles to be counted may be detachably placed in a holder 20 which is in turn detachably mounted upon stage 5.

Stage 5 may be then manually or automatically operated to pass one capillary tube 30 lengthwise under the beam from the source 6. The next adjacent tube 30 is similarly "scanned" over its length. This continues until all such tubes 30 in the holder 20 have been "scanned".

Source 6 preferably has a substantially "square" shaped filament 4 as shown in cross-section in FIG. 2. This filament 4 may be oriented perpendicular to the direction of travel of a capillary tube 30 along its length, as described hereinabove. Reference detector 8*a* may be conveniently mounted adjacent source 6 to measure its intensity. However, when reference detector 8*a* is employed, as described later herein, it is preferably located adjacent objective lens 7 to avoid the direct intensity of source 6 from overloading detector 8*a*. Iris 9 may reduce the overall size of the ray bundle to preferably be paraxial rays having a diameter substantially that of the interior bore of tube 30 after passing through collimating lens 11. This bundle of paraxial rays provide the light that each tube 30 passes through in order to be "scanned". This bundle passes through capillary tube 30 to objective lens 7. From objective lens 7 the light beam is reflected by mirror 14 to mirror or prism 13 and then into sample detector 8 through slit 15. Detector 8 is positioned to preferably be in the image plane of objective lens 7. By employing a highly collimated paraxial bundle, a particle may be detected whether in the upper, lower or middle portion of the bore of the capillary tube. The paraxial bundle provides a large depth of field to allow particles in any "height" position in the bore to be imaged on the detector 8 by the objective lens 7.

Sample detector 8 and reference detector 8*a* are preferably photovoltaic detectors whose current output is a function of the intensity of the light falling upon them. Sample detector 8 also preferably has a slit 15 immediately adjacent it. Slit 15 may be oriented parallel to the source filament, i.e., perpendicular to the capillary tubes (30) lengthwise direction of travel. Slit 15 reduces the amount of background or "noise" light detected by detector 8, as well as acting in conjunction with objective lens 7 to determine the smallest particle detectable, as more fully described later herein.

Capillary tube 30 is also preferably of a square cross-section. Such a square cross-section eliminates the "dead" detection areas along the outside edges of a circular cross-section capillary tube due to the lens effect of the curved walls of the circular capillary. The square cross-section capillary 30 has both an interior bore and exterior shape having a square cross-section.

Small particles of a preselected minimum size may be placed in capillary tube 30 and then scanned to count the number of such particles in the tube 30. Preferably, these small particles are biologic particles for use in testing the efficacy of chemotherapeutic agents; that is the tube 30 may be scanned to detect cell colonies in a tube 30 and thereby determine the efficacy of a chemotherapeutic agent or combinations of such agents as is described later herein.

Source 6 preferably emits white light, however a monochromatic source may also be employed. For both types of sources, the smallest size particle that may be detected may be determined by the width of slit 15 and the power of objective lens 7. The power of objective lens 7 may be selected to provide an image of the bore of the capillary tube that equals the size of detector 8 available along the length of the two edges of slit 15. The width of slit 15 may then effectively determine the diameter of the smallest particle detectable. Detector 8 is preferably positioned immediately behind slit 15 and by detecting changes in intensity of the direct or transmitted beam caused by the blocking action of the particles, detects and counts such particles.

When the slit 15 is positioned immediately in front of detector 8, the width of the slit is effectively reduced by the power of objective lens 7 when projected back onto the capillary tube 30. This reduced projected width determines the diameter or cross-sectional width of a particle that completely extends from one side of the slit to the other. This reduced projected width combined with the sensitivity of detector 8 may then determine the smallest particle detectable.

The maximum decrease in detected intensity caused by the blocking action of one particle occurs when the particle extends from one edge to the other edge of the slit. The amplitude of this decrease is related to the ratio of the amount of area obscured or blocked by the particle compared to the total slit area and to the relative opacity or translucence of the particle. When such a particle is "scanned" it preferably results in a detector signal having a sharp tipped peak when the particle is positioned between the slit edges.

Particles having a size less than the full width of the reduced projected width of the slit do not completely bridge the slit and therefore may result in detector signals having a flat top, or signals that are trapezoidal in shape. Depending upon the sensitivity of the detector 8, this reduction in intensity may still be detectable and thus the projected slit width and detector sensitivity may combine to determine the smallest particle detectable.

For particles having a size greater than the full width of the reduced projected width of the slit, this same trapezoidal shaped detector signal may result.

Preferably, the magnification of objective lens 7 is selected to produce a bore size projected at slit 15 that is slightly less than the full "length" of the slit. This reduces the need for the capillary tubes to be placed in exactly the same position to avoid part of the projected bore falling off the "length" of slit 15 and falling outside the active detection area of detector 8. Preferably, objective lens 7 has a power of 10× and slit 15 has a width of 0.1 millimeters resulting in a 10 micron diameter particle having a sharp tipped detector signal, as noted hereinbefore.

Alternatively, slit 15 may be placed between lens 11 and capillary tube 30. When slit 15 is employed in this position, iris 9 may be omitted. However, in this position the width of slit 15 must be about the same width as the smallest particle to be detected; again, the smallest size may also depend on detector sensitivity. For about 10 micron particles this may require a slit width of about 10 microns which is difficult to accurately fabricate.

However, any changes in intensity must be due to blocking by small particles and not due to fluctuations in intensity due to voltage fluctuations in the source's 6 voltage supply. To avoid such a problem with false indirections, it is presently preferred that source 6 be supplied by a regulated constant voltage DC supply. Alternatively, a second reference detector 8*a* may be employed to monitor the intensity of source 6 and an unregulated voltage supply employed. This second reference detector's output may then be compared with that of the first detector to determine intensity changes caused by small particles blocking light.

Figure 3:
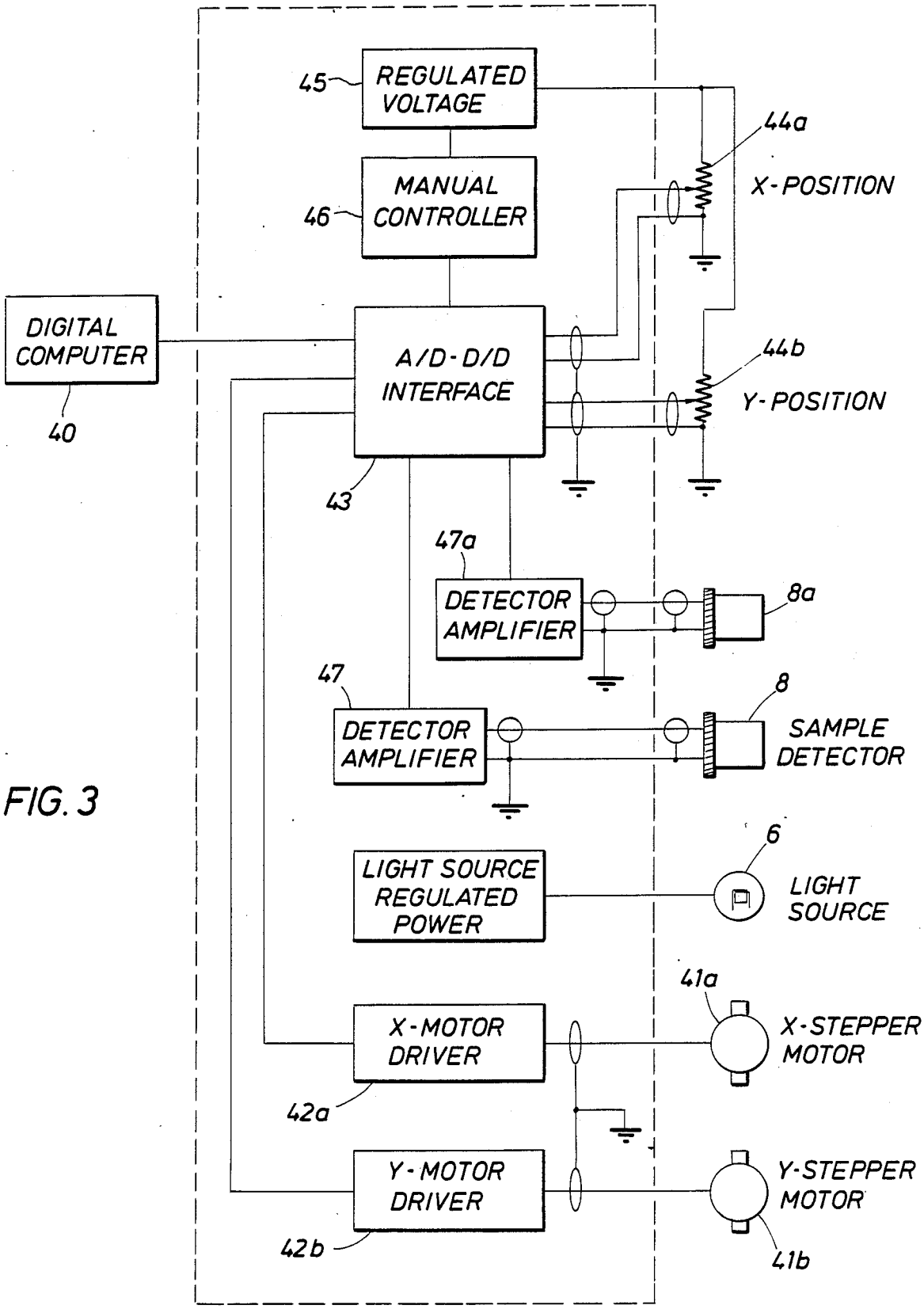
FIG. 3 depicts a block diagram of the electronics of the apparatus of FIG. 1.

Referring now to FIG. 3, there may be seen a simplified electrical block diagram of the apparatus depicted in FIG. 1. The output of detector 8 and detector 8*a* (when employed) may be suitably amplified as described later herein and then digitized for storage by a small digital computer 40. Such a small digital computer 40 may also be employed to control the movement of stage 5 of the apparatus so that each tube 30 on holder 20 on stage 5 is automatically "scanned" and the data corresponding to each position of the "scan" of the tube 30 stored in the memory of such a computer. The computer 40 may also be programmed to relate peak size and shape to the number and/or size of particles being scanned. Later scans may also be made to determine the growth, if any, of such biologic particles. In this manner the apparatus may automatically determine the efficacy of chemotherapeutic agents.

The digital computer 40 may record the digitized "X" and "Y" position of each capillary tube 30 for each position of the stage 5, as well as the digitized signal from detector 8 (or the difference between detectors 8 and 8*a*) at each of these positions. In this manner, the computer's raw data is in essence the magnitude of a signal representing the intercepting of a light beam by an object and the position of that object.

The digital computer 40 also may control the positioning of the stage 5. This may be accomplished by having a conventional precise lead screw (not shown) to control the "X" movement of stage 5 and a second duplicate precise lead screw to control the "Y" movement of stage 5. These two lead screws may be each in turn appropriately connected to stepper motors 41*a*, 41*b*. The two stepper motors 41*a*, 41*b* may be, in turn, electrically connected to stepper motor controllers 42*a*, 42*b*. The two stepper motor controllers 42*a*, 42*b* may be suitably connected to the digital computer 40 via an interface unit 43 so that the computer 40 may control the rotation of the "X" and "Y" stepper motors and thereby the "X" and "Y" position of stage 5.

The stage 5 may also include DC linear potentiometers 44*a*, 44*b* associated with the "X" and "Y" directions. These potentiometers 44*a*, 44*b*, when suitably connected to stage 5, may provide a direct positive indication of the X and Y position of the stage 5. These potentiometers 44*a*, 44*b* may be suitably electrically interconnected with the computer 40 to provide this location information to the computer 40. Thus the computer 40 may count the number of steps it tells the stage to move and know where the stage should be based upon where the stage was initially. It may then compare this calculated position to the stage's actual position as indicated by the position potentiometers 44.

The signal representing an object in the light beam is first digitally smoothed by the computer 40. To allow for subsequent scans, the significant features are normalized to one or more relative positions. This allows comparison of and subtraction of an initial scan from later scans to identify features which have survived and grown. The computer 40 may also integrate the area of any peaks for these features to determine how large any growth has become.

The presently preferred embodiment of the present invention is constructed around an inverted microscope that is commercially available from the Olympus Corporation of America (Model CK, Olympus inverted microscope), and employs a 10× objective lens 7 and 10× eye piece 12. The base of this microscope is removed and its stage is replaced with a special stage 5.

The special stage 5 has two conventional high precision lead screws having a movement of about 2 millimeters per revolution. One such lead screw is for the "X" direction of movement and the other lead screw is for the "Y" direction of movement, as noted hereinbefore. Each lead screw is driven by a stepper motor 41*a*, 41*b*, requiring about 25,000 steps per revolution.

The stage 5 is further designed to accommodate a special capillary tube holder 20, that is about 4.5 inches by about 3.4 inches by about 0.1 inches thick. Each tube holder 20 is precisely machined to be replaceable to the same position in the stage 5. This is accomplished by spring loading the holder 20 against the frame of stage 5 along two perpendicular machined surfaces of the holder 20. The holder 20 is machined to precisely and repeatably hold eighteen square capillary tubes 30.

A photovoltaic detector such as a commercially available S13371010 BR from Hamamatsu, or equivalents, may be employed. The detector 8 is suitably mounted with an adjustable slit 15 in the vertical photo tube of the microscope. The alternate photovoltaic detector 8*a* (when used) may be mounted on the housing adjacent the source (as depicted in FIGS. 1 and 2) or preferably adjacent the objective lens 7 to detect changes in the intensity of source 6.

The presently preferred capillary tube 30 has a square cross-section with an inside width (in the bore) of about 1 millimeter and a length of about 3.75 inches. The interior bore is of uniform width and has been found particularly suitable for counting small particles as small as about 10 microns.

However, for these smaller sized particles, some consideration should be given to reducing the interior bore of the capillary tube to avoid "stacking" of such small particles across the bore. Such stacking, if allowed, will result in erroneous particle counts since a whole line of "stacked" particles can potentially be counted as only one particle.

An alternative solution to the reduction of the capillary bore size for very small particles is to rotate the capillary tube about its longitudinal axis and then rescan the tube. This will require modification to be made to tube holder 20 and stage 5. The number of particles may then be reconstructed (using conventional imaging techniques) by the digital computer. This imaging technique process may require a plurality of scans, each at different angular rotations of the capillary about its longitudinal axis.

The presently preferred digital computer is a Hewlett-Packard 9816 computer. The interface unit is a specially designed analog-to-digital and/or digital-to-analog circuit. Such an interface unit is dependent upon the digital computer selected and the other electronic components selected, as described later herein. The digital computer is suitably programmed to perform the hereinbefore described functions, as a function of the interface unit input and output signal levels and polarities. A block diagram of the presently preferred interface unit is depicted in FIG. 4.

Figure 4:
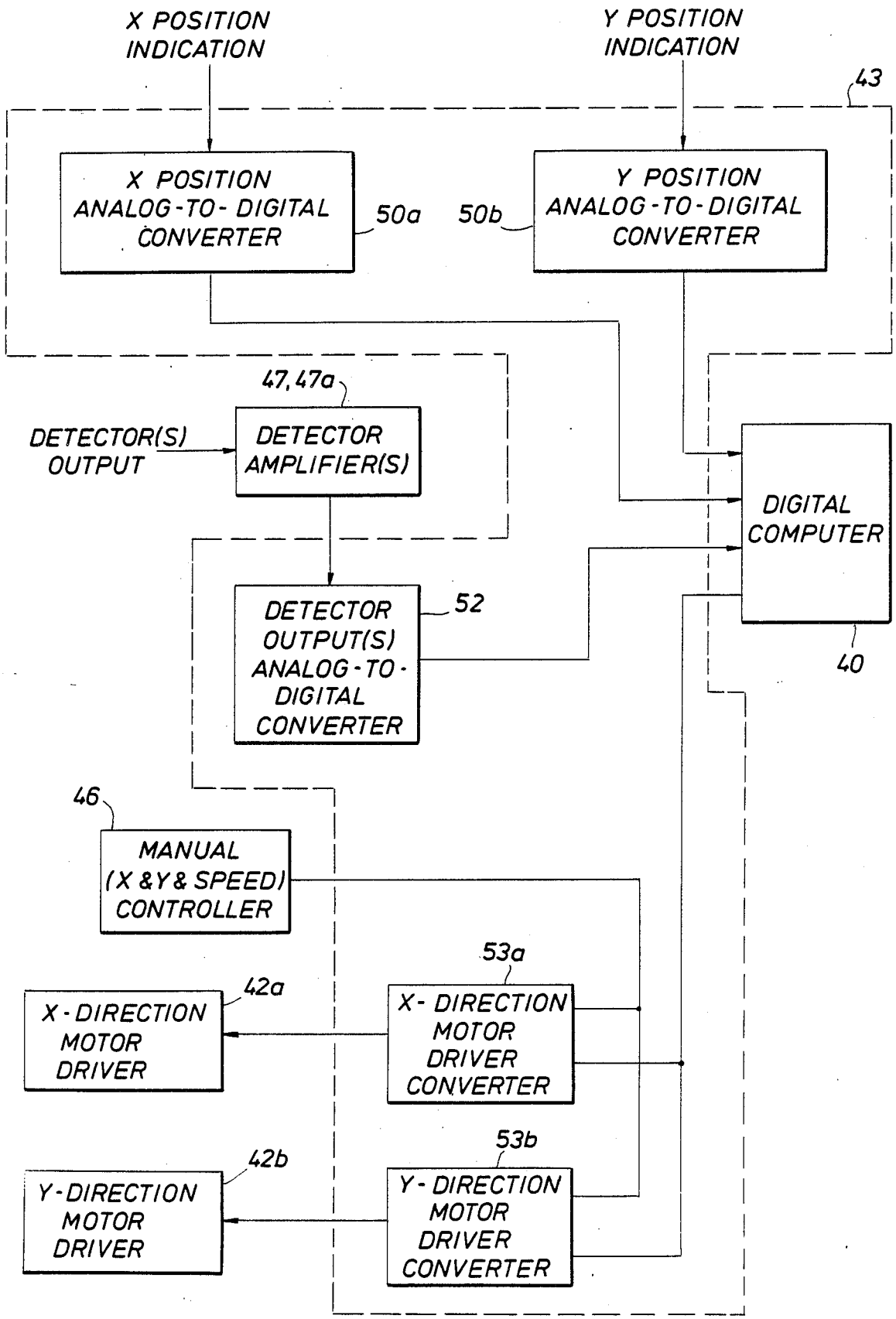
FIG. 4 depicts a block diagram of a portion of FIG. 3.

Referring now to FIG. 4, there may be seen a simplified block diagram of interface unit 43 of FIG. 3. More specifically, there can be seen the position indicator analog-to-digital converters 50*a* and 50*b* and motor driver converters 53*a* and 53*b*, for X and Y directions respectively. The interconnection of the motor driver converters with the manual controller 46 and computer 40 is also depicted. The actual position from the position indicators may be supplied directly to the manual controller or indirectly through computer 40 as depicted in FIG. 4. Also shown is an analog-to-digital converter 52 for the output of the detector (or detectors).

Figure 5:
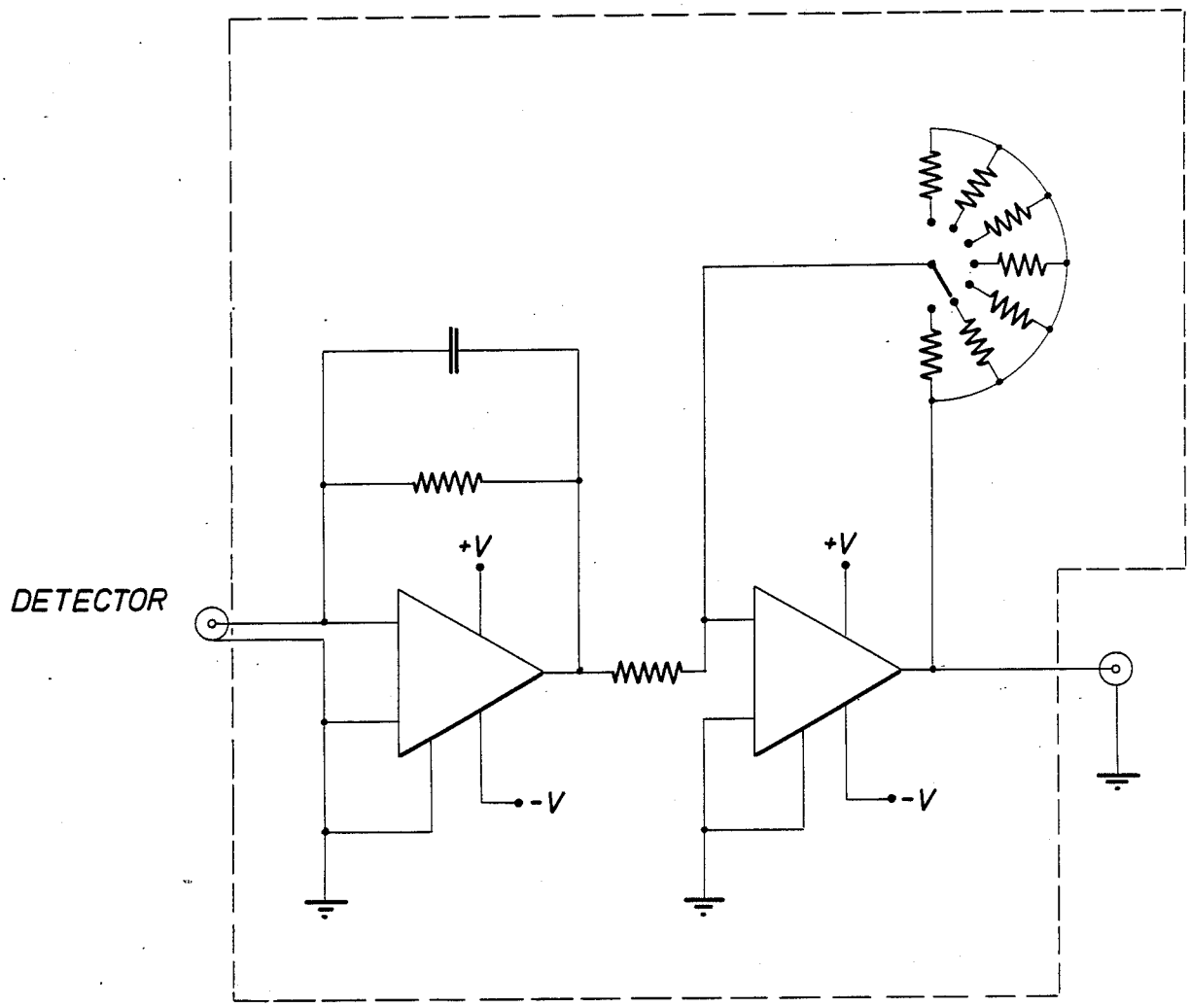
FIG. 5 depicts a block diagram of a different portion of FIG. 3.

The presently preferred detection circuitry is depicted in FIG. 5. This circuitry employs two AD515JH operational amplifiers, operating in the "inverting cascade" mode. The sample detector signal is input directly to the inverting input of the first amplifier via a common shield coaxial cable. Gain and integration of the first amplifier is accomplished by using low noise, fixed resistive and capacitive feedback; no potentiometers are used.

The output of the first amplifier is coupled to the inverting input of the second amplifier through a resistor. The second amplifier contains no integration and is gain selectable through a multiposition switch to which various valued fixed gain feedback resistors are attached. Output of the second amplifier is interpreted as percent opacity once digitized by the interface unit.

When two detectors are employed (reference and sample detectors) both detectors may be connected to their respective operational amplifiers in the "current" mode. The amplifiers output a linear DC signal to a divider circuit (not shown). The divider outputs a DC signal proportional to the difference of the outputs of the detector amplifiers. The reference detector compensates electronically for changes in light source intensity while the sample detector measures the light emanating from the sample.

The presently preferred embodiment orients the stage so that the "X" direction corresponds to the scanning along the length of a capillary tube. The "Y" direction thus corresponds to the tube number in the holder. The X and Y directions are incremented in small "steps", such that the total movement of the stage in either the X or Y direction consists preferably of about 5,000 such steps. Thus, a "scan" of a tube 30 involves collecting data at each of these 5,000 steps. This number of steps is large enough to provide a resolution limited by the optics and not by the movement of the stage while being small enough to avoid storing a lot of unnecessary data points in the computer memory system. However, the system may employ up to 10,000 steps. The position of the stage is sensed by the computer through the use of 10 volt DC linear potentiometers such as those available from Bourns Instruments.

The stepper motors and motor drivers are preferably Sigma® model 3010A motors and drivers, or they may be Compumotor model M57-51, or other equivalents.

The hereinabove described presently preferred embodiment has been used to detect the growth or lack of growth of tumor cells in response to treatment of the cells with proposed chemotherapeutic agents. A solution of the cells and proposed chemotherapeutic agent(s) is introduced into a capillary tube. The tube is then placed in a holder, along with other capillary tubes similarly filled. Each tube in this holder is then scanned. The data about the type of cell and chemotherapeutic agent(s) may also be entered into the computer for each tube and may be stored along with the initial scan data. Depending upon the cell growth speed, a later scan may be made 24 hours following the initial scan to determine what chemotherapeutic agents are effective and prevent cell growth. This later scan has the initial scan data subtracted to remove artifacts and/or impurities from the cell growth data. Additional scans may be made later, if desired. For human cancers, later scans are normally 72–96 hours after the initial scan.

Many other variations and modifications may be made in the apparatus and techniques hereinbefore described, by those having experience in this technology, without departing from the concept of the present invention. Accordingly, it should be clearly understood that the apparatus and methods depicted in the accompanying drawings and referred to in the foregoing description are illustrative only and are not intended as limitations on the scope of the invention.

What is claimed is:

1. A method for detecting and counting a small particle of at least a preselected size, comprising:
   generating a paraxial beam of light;
   moving said small particle substantially perpendicularly through said beam; and
   detecting and measuring the changes in intensity of said beam caused by said particle.

2. A method as described in claim 1, wherein said detecting and measuring is in an area functionally related to said preselected size.

3. A method as described in claim 2, further comprising providing a suitable transparent container for said particle.

4. Apparatus for detecting and counting a plurality of small particles of at least a preselected size, comprising:
   means for generating a paraxial beam of light;
   means for moving said small particles substantially perpendicularly through said beam; and
   means for detecting and measuring the changes in intensity of said beam caused by said particles.

5. Apparatus for detecting and counting a plurality of small particles of at least a preselected size, comprising:
   carrier means for containing said small particles;
   mounting means for releasably containing said carrier means;
   transporting means for releasably holding and moving said mounting means;
   source means for providing light to illuminate and pass through said carrier means;
   lens means for providing enlarged images of said small particles;
   detector means for detecting said images and generating data representative thereof; and
   slit means for determining said preselected size in functional relationship with said detector means.

6. The apparatus described in claim 5, further comprising controller means for controlling the position and movement of said transporting means.

7. The apparatus described in claim 6, further comprising position means for providing data on the location of said transporting means.

8. The apparatus described in claim 7, further comprising computer means for controlling said controller means and storing data from said position means and said detector means.

9. A method for detecting and counting organisms that form colonies comprising:
   immobilizing and containing said organisms;
   generating a paraxial beam of light;
   passing said organisms substantially perpendicularly through said beam; and
   detecting and measuring the changes in intensity of said beam after passing through said organisms.

10. A method as described in claim 9, further comprising recording said changes in intensity of said beam.

11. A method as described in claim 10, further comprising culturing said organisms with preselected materials and substances.

12. A method as described in claim 11, further comprising:
   repeating said passing and said detecting and measuring step; and determining the changes in numbers of said organisms.

13. A method for determining the efficacy of a chemotherapeutic agent, comprising:

providing a plurality of tumor cells;

mixing said tumor cells and said chemotherapeutic agent;

immobilizing and containing said cells and agent;

generating a paraxial light beam;

passing said cells substantially perpendicularly through said beam;

culturing said cells; and repeating said passing, said detecting and measuring, and said recording steps.

* * * * *